United States Patent
Koulikov et al.

(10) Patent No.: US 7,777,886 B2
(45) Date of Patent: Aug. 17, 2010

(54) OPTICAL SYSTEM INCLUDING A WEAK LENS AND A BEAM TRANSLATION PLATE FOR SELECTIVELY COUPLING TO THE LOWEST ORDER MODE OF AN OPTICAL RESONATOR

(75) Inventors: Serguei Koulikov, Mountain View, CA (US); Bruce A. Richman, Sunnyvale, CA (US); Dmitri Davydov, Kanata (CA)

(73) Assignee: Picarro, Inc., Sunnyvale, CA (US)

( * ) Notice: Subject to any disclaimer, the term of this patent is extended or adjusted under 35 U.S.C. 154(b) by 634 days.

(21) Appl. No.: 11/708,994

(22) Filed: Feb. 21, 2007

(65) Prior Publication Data
US 2007/0195434 A1 Aug. 23, 2007

Related U.S. Application Data

(60) Provisional application No. 60/776,396, filed on Feb. 23, 2006.

(51) Int. Cl.
*G01N 21/00* (2006.01)
(52) U.S. Cl. ............ 356/437; 250/573; 250/576; 356/432; 356/440; 356/461; 359/809; 359/813; 359/822
(58) Field of Classification Search ............ 356/432, 356/437, 440, 470, 300, 451, 461, 468; 250/573–576; 359/809–813, 822
See application file for complete search history.

(56) References Cited

U.S. PATENT DOCUMENTS 5,291,265 A  3/1994  Kebabian
5,313,270 A  5/1994  Fishman et al.
5,912,740 A  6/1999  Zare et al.
6,084,682 A *  7/2000  Zare et al. ............ 356/437
6,563,583 B2  5/2003  Ortyn et al.
6,816,323 B2 * 11/2004  Colin et al. ............ 359/819
7,012,696 B2 *  3/2006  Orr et al. ............ 356/454
2005/0168826 A1  8/2005  Koulikov et al.

OTHER PUBLICATIONS

"Description of Prior Sale" Feb. 23, 2005.
Paul, Joshua B. "Ultrasensitive absorption spectroscopy with a high-finesse optical cavity and off-axis alignment." Sep. 20, 2001. vol. 40, No. 27. Applied Optics.

* cited by examiner

*Primary Examiner*—Gregory J Toatley, Jr.
*Assistant Examiner*—Iyabo S Alli
(74) *Attorney, Agent, or Firm*—Lumen Patent Firm

(57) ABSTRACT

Improved optical alignment precision to a passive optical cavity is provided by including a combination of a weak focusing element and a translation plate in the input coupling optics. Adjustment of positions and angles of these optical elements, preferably after all other input optical elements are fixed in place, advantageously provides for high-precision optical alignment to the cavity, without requiring excessively tight fabrication tolerances. Fabrication tolerances are relaxed by making the optical power of the weak focusing element significantly less than the optical power of a strong focusing element in the input optics. The position and angles of the beam with respect to the cavity can be adjusted, as can the size of the beam at the cavity. Differential adjustment of the beam size in two orthogonal directions (e.g., tangential plane and sagittal plane) at the cavity can also be provided.

20 Claims, 4 Drawing Sheets

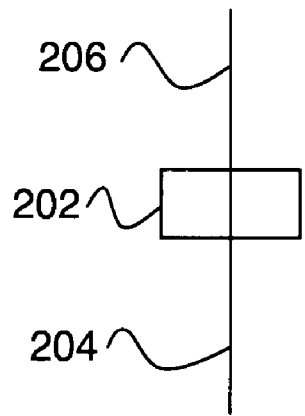 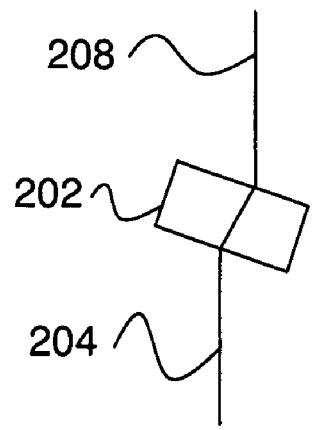 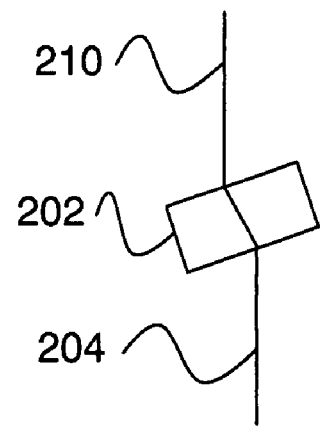
Fig. 2a　　　　　　Fig. 2b　　　　　　Fig. 2c
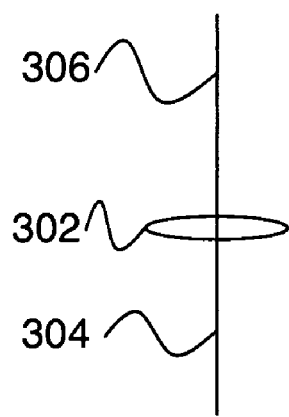 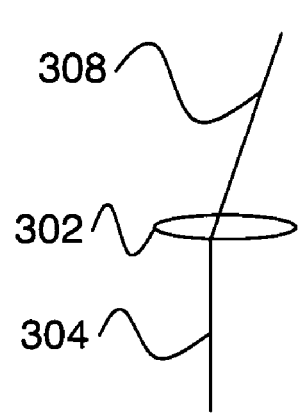 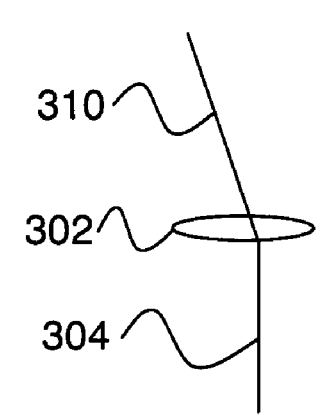
Fig. 3a　　　　　　Fig. 3b　　　　　　Fig. 3c

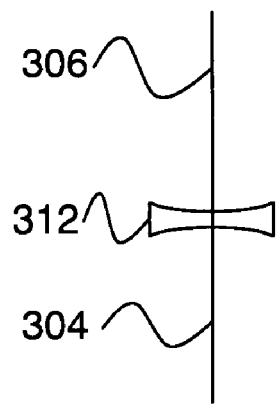
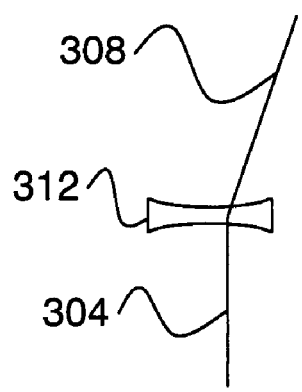
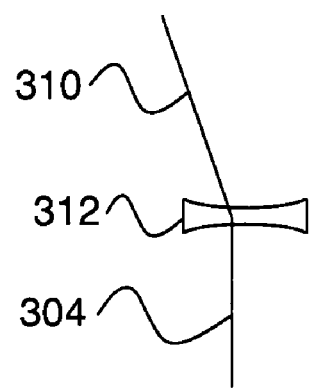
Fig. 3d    Fig. 3e    Fig. 3f
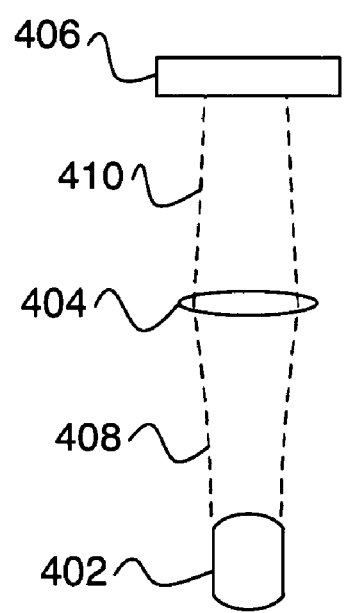
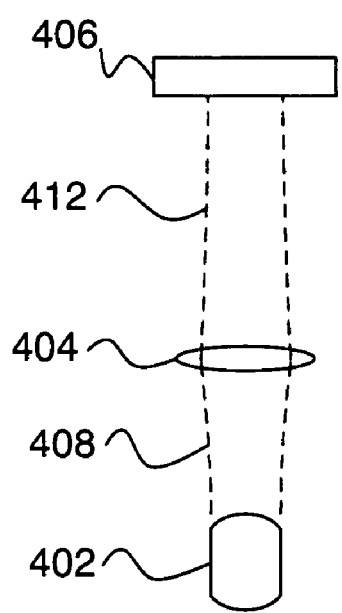
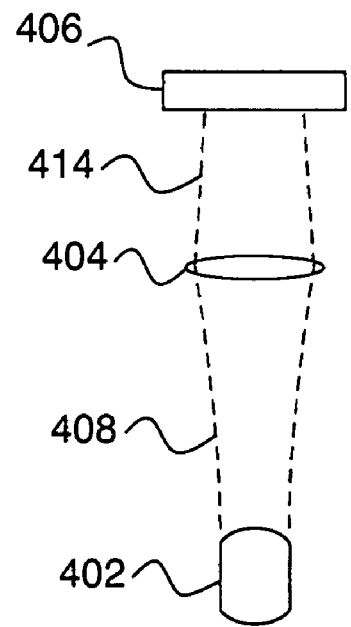
Fig. 4a    Fig. 4b    Fig. 4c

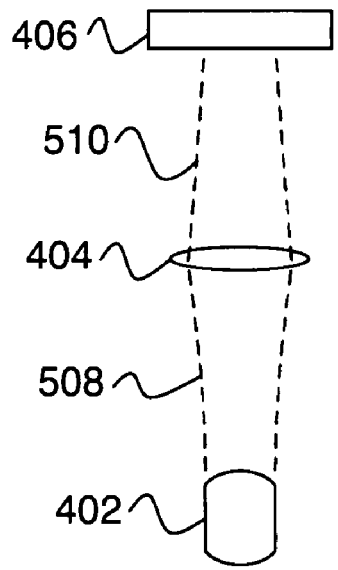
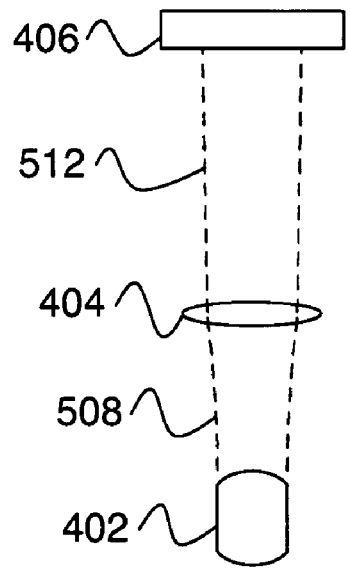
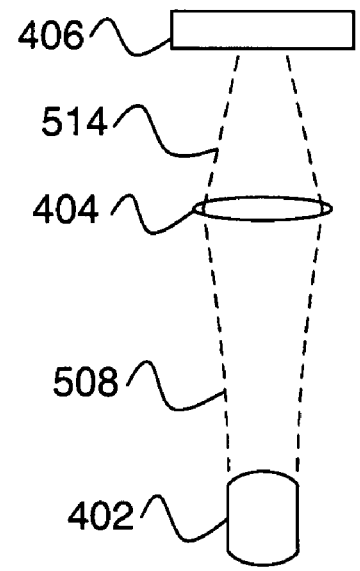
Fig. 5a        Fig. 5b        Fig. 5c
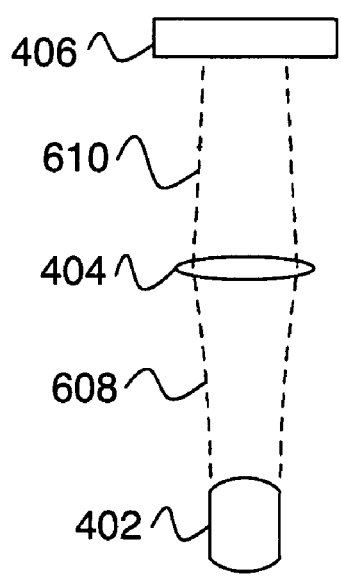
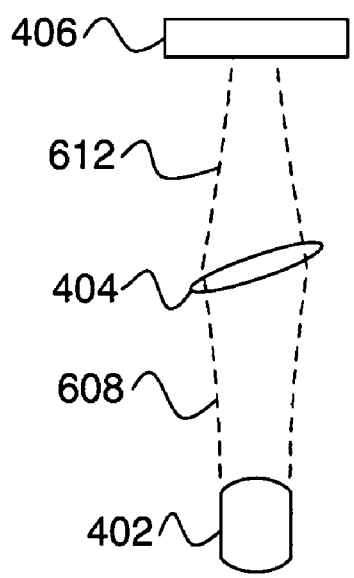
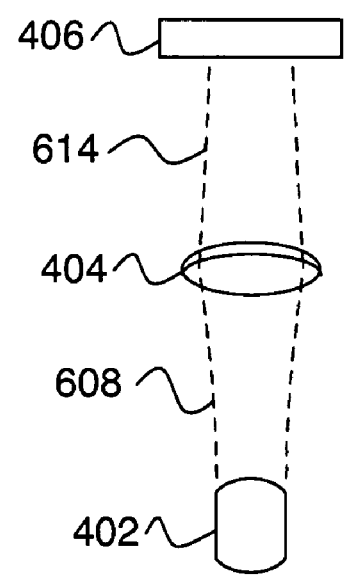
Fig. 6a        Fig. 6b        Fig. 6c

OPTICAL SYSTEM INCLUDING A WEAK LENS AND A BEAM TRANSLATION PLATE FOR SELECTIVELY COUPLING TO THE LOWEST ORDER MODE OF AN OPTICAL RESONATOR

CROSS REFERENCE TO RELATED APPLICATIONS

This application claims the benefit of U.S. provisional patent application 60/776,396, filed on Feb. 23, 2006, entitled "Methods and Apparatus for Improved Cavity Ring-down Spectroscopy", and hereby incorporated by reference in its entirety.

FIELD OF THE INVENTION

This invention relates to optical alignment in connection with cavity-enhanced spectroscopy.

BACKGROUND

Optical spectroscopy entails passing optical radiation through a sample, often referred to an analyte, and inferring properties of the analyte from measurements performed on the optical radiation. For example, trace gas detection can be spectroscopically performed by performing measurements to detect the presence or absence of spectral absorption lines corresponding to the gas species of interest. Spectroscopy has been intensively developed over a period of many decades, and various ideas have been developed to improve performance.

One such idea can be referred to as cavity-enhanced spectroscopy, in which the analyte is disposed within an optical cavity (i.e., an optical resonator). The cavity can enhance the interaction between the analyte and the optical radiation, thereby improving spectroscopic performance. For example, in cavity ring-down spectroscopy (CRDS), the absorption is measured by way of its effect on the energy decay time of an optical cavity. Increased absorption decreases the decay time, and vice versa. As another example, cavity enhanced absorption spectroscopy (CEAS) entails the use of an optical cavity to increase the sensitivity of absorption spectroscopy, in connection with direct absorption measurements.

One of the noteworthy features of cavity-enhanced spectroscopy is that issues of optical alignment can arise which differ in important respects from alignment issues in other branches of optics. More specifically, a key alignment issue faced in many implementations of cavity enhanced spectroscopy is selectively exciting the lowest order mode of a passive optical cavity with an external optical source while minimizing excitation of the higher order modes of the cavity. The theoretical condition for providing such selective mode excitation is well known in the art, and is often referred to as "mode matching". For example, suppose radiation in the lowest order mode of an optical cavity would be emitted from the cavity as a Gaussian beam having certain parameters (e.g., waist size $w_0$, waist position $z_0$) along a beam axis L. In this example, radiation provided to the cavity as a Gaussian beam with waist size $w_0$ and waist position $z_0$ along beam axis L is mode matched to the lowest order mode of the resonator, and will selectively excite the lowest order mode of the cavity.

Although the theoretical condition for mode matching is well known, practical issues such as assembly tolerances and optical component tolerances can cause substantial difficulties. In this context, it is important to note that the passive cavity alignment problem is a much less forgiving single-mode alignment problem than the extensively explored problem of coupling to a single mode optical fiber or waveguide. The reason for this difference can be appreciated with a simple example where practical imperfections are assumed to cause a 1% loss of power coupled to the desired mode.

In the case of fiber or waveguide coupling, this 1% of the incident light that does not couple to the desired mode is lost from the system. There is typically no degradation of performance other than the 1% loss. In the case of coupling to a passive spectroscopic cavity, the 1% of the incident light that does not couple to the desired lowest order mode can couple to one or more of the higher order modes of the cavity. Such excitation of undesired cavity modes can seriously degrade spectroscopic performance, by effectively raising the noise floor. Such an effective increase in noise is typically a much more significant performance degradation than the 1% signal loss entailed by the above assumption.

Although the importance of achieving the mode matching condition is well known (e.g., as indicated in U.S. Pat. No. 5,912,790), specific methods for providing mode matching to a passive cavity in practice do not appear to have been explicitly considered in the art. US 2005/0168826 is an example where a somewhat related alignment problem is considered. In this work, an alignment system including a weak lens provides coupling of a source to a single mode waveguide. Coupling efficiency to the waveguide is enhanced by adjusting the position and angles of the weak lens during assembly. Another somewhat related problem of alignment has been considered in U.S. Pat. No. 6,563,583, where alignment is required to a multi-pass cell as opposed to an optical cavity. In this work, active feedback control is employed to measure and correct beam position and angle errors.

However, it is preferable to provide the level of alignment precision needed for cavity enhanced spectroscopy with an optical system having no moving parts, to reduce cost and simplify the resulting system. Accordingly, it would be an advance in the art to provide improved mode matching to a passive optical cavity while allowing for fabrication and assembly tolerances.

SUMMARY

Improved optical alignment precision to a passive optical cavity is provided by including a combination of a weak focusing element and a translation plate in the input coupling optics. Adjustment of positions and angles of these optical elements, preferably after all other input optical elements are fixed in place, advantageously provides for high-precision optical alignment to the cavity, without requiring excessively tight fabrication tolerances. Fabrication tolerances are relaxed by making the optical power of the weak focusing element significantly less than the optical power of a strong focusing element in the input optics. The position and angles of the beam with respect to the cavity can be adjusted, as can the size of the beam at the cavity. Differential adjustment of the beam size in two orthogonal directions (e.g., tangential plane and sagittal plane) at the cavity can also be provided.

BRIEF DESCRIPTION OF THE DRAWINGS

FIGS. 2a-c show adjustment of beam position by tilting a beam translation plate.

FIGS. 3a-f show adjustment of beam angle by laterally translating a weak lens.

FIGS. 4a-c show adjustment of beam size by longitudinally translating a weak lens.

FIGS. 5a-c show another example of adjustment of beam size by longitudinally translating a weak lens.

FIGS. 6a-c show differential adjustment of beam size in the tangential and sagittal planes by tilting a weak lens.

DETAILED DESCRIPTION

Figure 1:
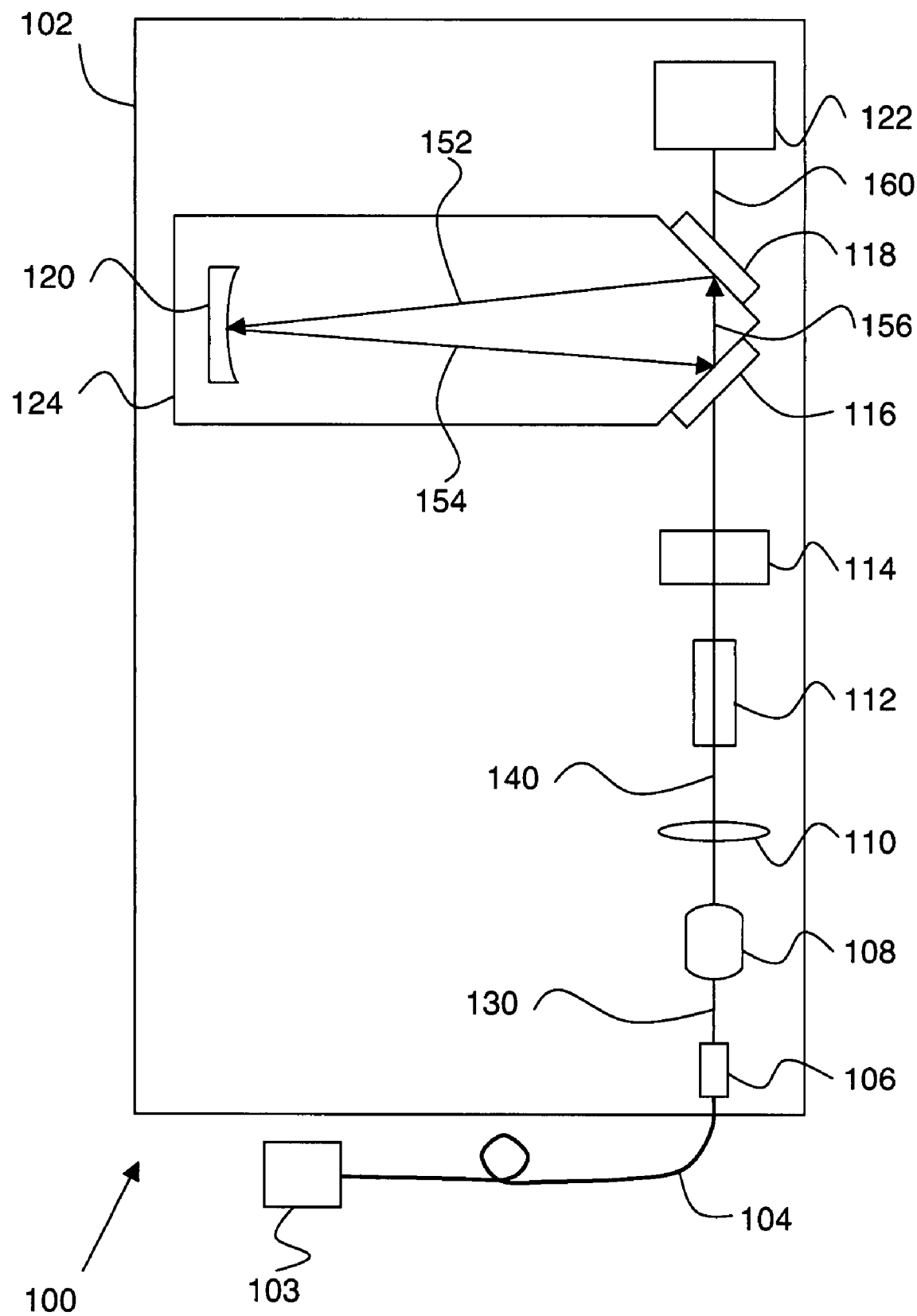
FIG. 1 shows a cavity enhanced spectroscopy system according to an embodiment of the invention.

FIG. 1 shows a cavity enhanced spectroscopy system 100 according to an embodiment of the invention. In this example, various optical components are affixed to a bench 102. Bench 102 can be made of any sufficiently stable and strong material, and preferably has a low coefficient of thermal expansion (CTE). Accordingly, bench 102 preferably includes FeNi36, which is a generic designation for the steel alloy known in trade as Invar®. A first beam of optical radiation 130 is emitted from a fiber pigtail 106 coupled to an optical fiber 104 which receives radiation from a laser diode 103. In this example, fiber 104 is preferably polarization-maintaining (PM) fiber, since it is desirable to fix the polarization of the first light beam. More specifically, it is preferable for the polarization to be TE at the cavity (i.e., electric field parallel to the surfaces of mirrors 116 and 118) because cavity loss can be made lower for TE polarization than for TM polarization, and for the polarization emitted from fiber 104 to be set accordingly. Isolator 112, if present, may change the state of polarization, and any such change should be accounted for. It is also preferred for the end face of fiber pigtail 106 to be angled, to reduce back-reflection into source 103 along fiber 104.

However, practice of the invention does not depend critically on details of the optical source configuration, and any source of spatially coherent single-mode optical radiation having a temporal coherence suitable for the kind of spectroscopy being employed (e.g., narrow linewidth for continuous-wave (CW) CRDS, wide linewidth for pulsed CRDS) can be employed. Suitable sources include, but are not limited to: lasers, diode lasers, standard single mode fiber (SMF) coupled lasers, SMF coupled diode lasers, PM fiber coupled lasers, and PM fiber coupled diode lasers.

First beam 130 is received by a strong focusing element 108 which provides a second beam 140. Second beam 140 passes in succession through a weak focusing element 110, an optional isolator 112, and a translation plate 114 before impinging on resonator mirror 116. Mirrors 116, 118 and 120 form an optical resonator (also referred to as an optical cavity). In this example, the cavity is a ring resonator, as indicated by the cavity round trip path having segments 152, 154, and 156. The resonator mirrors are affixed to a mechanical cavity housing 124, which provides stable mechanical support to the resonator mirrors. Mechanical housing 124 can be made of any sufficiently stable and strong material, and preferably has a low CTE which is preferably matched to the CTE of bench 102. Accordingly, mechanical housing 124 also preferably includes FeNi36 (Invar®). Radiation is emitted from the cavity as an output beam 160, which is received by a detector 122. The system of FIG. 1 is suitable for performing various kinds of cavity enhanced spectroscopy, such as cavity ring-down spectroscopy (CRDS) and cavity enhanced absorption spectroscopy (CEAS). It is also suitable for performing multi-pass absorption spectroscopy where the optical cavity is replaced by a multi-pass cell, since multi-pass cells often require precise input beam alignment. Multi-pass cells can often be treated as optical cavities for purposes of analysis The example of FIG. 1 shows a specific cavity configuration for illustrative purposes, and practice of the invention does not depend critically on the resonator configuration. In particular, the invention is applicable to both ring cavities having three or more mirrors and to standing wave cavities having two or more mirrors.

The example of FIG. 1 also show an optional isolator 112. The purpose of isolator 112 is to prevent optical feedback from the cavity from propagating back into fiber 104 and to source 103, since such feedback can impair performance.

The cavity formed by mirrors 116, 118, and 120 has a lowest order mode and also supports one or more higher order modes. It is important for second beam 140 to selectively excite the lowest order mode while minimizing excitation of the higher order modes as much as possible. Accordingly, the combination of strong focusing element 108 and weak focusing element 110 should provide an exact or approximate mode match of second beam 140 to the lowest order mode of the optical resonator. In practice, achieving an exact mode match is typically not possible, so the approximate mode match is preferably made as close to exact as possible, given assembly and fabrication tolerances.

A key aspect of the present invention can be better appreciated by noting that it is possible, in principle, to mode match second beam 140 to the lowest order cavity mode using strong focusing element 108 alone, and omitting translation plate 114 and weak focusing element 110. However, the resulting positioning tolerances on strong focusing element 108 tend to be unattainable in practice. Accordingly, a key idea of the present invention is that by introducing "extra" elements (i.e., weak focusing element 110 and translation plate 114), the assembly tolerances on the strong focusing element (and throughout the mode matching subsystem) can be relaxed, while still providing a very precise mode match of second beam 140 to the lowest order cavity mode. In particular, positions and angles of weak focusing element 110 and of translation plate 114 can be adjusted during assembly to minimize excitation of higher order modes (while coupling to the lowest order mode), preferably after the positions of the cavity, strong focusing element 108, and fiber pigtail 106 have all been fixed.

To accomplish this purpose, it is important that weak focusing element 110 be weak relative to strong focusing element 108. The optical power of an optical element (in diopters) is 1/f, where f is the focal length in meters. The focal length and power are positive quantities for positive focusing elements, and are negative quantities for negative focusing elements. Typically, strong focusing element 108 is a positive lens or mirror (e.g., a collimator) since it is typically preferable to approximately collimate the diverging beam provided by most optical sources prior to any other operations on the beam. In unusual situations, a negative strong focusing element 108 can be employed. Weak focusing element 110 can be either positive or negative. Let the optical powers of the weak and strong focusing elements respectively be denoted as $d_w$ and $d_s$. Then $|d_w|$ is substantially less than $|d_s|$, and preferably $0.01|d_s|<|d_w|<0.2|d_s|$.

The limits of the preferred range can be better appreciated by considering the following two cases. If the weak focusing element is too weak, its effect on the optical beam may be too small to provide the adjustment range required to compensate for assembly and fabrication tolerances, which is undesirable. However, if the weak focusing element is too strong, its alignment tolerances will be comparable to those of the strong focusing element, which is also undesirable. The alignment precision required for a focusing element to provide a given level of beam positioning precision at the cavity scales roughly as the focal length of the focusing element. Thus a weak focusing element having a focal length 10× the focal length of a strong focusing element will have roughly a 10× larger alignment tolerance than the strong focusing element.

Similarly, the translation plate 114 must be thick enough to provide adequate displacement of beam 140 through angular adjustment of the plate, but not so thick that the displacement is too sensitive to the angular adjustment. Usually, the surfaces of the translation plate will be parallel or nearly parallel, in which case rotation of the plate displaces the beam 140 but does not (significantly) change its direction. If the translation plate has a substantial wedge angle between the input and output surfaces, then rotation will change both the displacement and angle of beam 140.

Translation of the weak focusing element 110 changes both the angle of beam 140 and its displacement at the cavity mirror. A pure change in angle at the cavity mirror is accomplished by simultaneous adjustment of the weak focusing element and the translation plate. Since the translation plate will usually have (nearly) parallel surfaces, a pure change in position of the beam at the cavity mirror is, in that case, accomplished by adjustment of only the translation plate.

Strong focusing element 108 can be a single optical element, or can be a combination of any number of optical elements (e.g., lenses and/or mirrors) having a "strong" optical power as described above. Similarly, weak focusing element 110 can be a single optical element, or can be a combination of any number of optical elements (e.g., lenses and/or mirrors) having a "weak" optical power as described above. It is preferable for strong focusing element 108 to be CTE matched to bench 102. In one design, strong focusing element 108 includes two fused silica lenses in series and in close proximity, having a combined focal length of about 8 mm and acting as a collimator. In this design, the weak focusing element is a single lens which can have a focal length from about 20 mm to about 200 mm (or from about −200 mm to about −20 mm).

Translation plate 114 is a transparent plate having planar and parallel or nearly parallel input and output faces. The main purpose of translation plate 114 is to provide adjustment of the position of second beam 140 at the input to the optical cavity (i.e., at mirror 116). Translation plate 114 can be made of any optical material. Suitable materials include glass and fused silica.

In practice, the positions of fiber pigtail 106, strong focusing element 108 and the cavity (i.e., mirrors 116, 118 and 120) are preferably fixed during a first assembly phase. If isolator 112 is present, its position is preferably also fixed during the first assembly phase. The positions and angles of weak focusing element 110 and translation plate 114 are adjusted to minimize excitation of higher-order cavity modes in a second assembly phase. Such adjustment is preferably performed by lighting up fiber 104 to excite the cavity and directly measuring the excitation of the higher-order modes. Positions and angles of weak focusing element 110 and translation plate 114 can then be adjusted to minimize the measured excitation of higher-order cavity modes. Once a minimum level of higher order mode excitation is achieved, the positions and angles of elements 110 and 114 are fixed.

The combination of weak focusing element 110 and translation plate 114 advantageously provides a large number of degrees of freedom to employ in optimizing coupling to the lowest order cavity mode. We have found that such extra degrees of freedom are sufficiently helpful for optimizing cavity coupling to warrant the use of two elements for beam adjustment, even though the total number of optical elements could be reduced by employing only a single beam adjustment element.

Relevant degrees of freedom (DOF) include the following: a) angular pitch and yaw of adjustment plate 114 with respect to beam 140, primarily for adjusting the lateral position of second beam 140 with respect to the cavity (2 DOF); b) lateral translation of weak focusing element 110 with respect to beam 140, primarily for adjusting the pitch and yaw angles of second beam 140 with respect to the cavity (2 DOF); c) longitudinal translation of weak focusing element 110 with respect to beam 140, primarily for adjusting the waist position of beam 140 with respect to the cavity (1 DOF); and d) angular pitch and yaw of weak focusing element 110 with respect to beam 140, primarily for providing a differential adjustment of beam waist position relative to the cavity in the tangential and sagittal planes (1 DOF). FIGS. 2a-6c show simplified examples of how these degrees of freedom can provide the adjustments indicated above.

FIGS. 2a-c show adjustment of beam position by tilting a beam translation plate. In each of these examples, an input beam 204 passes through a translation plate 202. Tilting of plate 202 displaces beam 204 by refraction at the input and output surfaces, by a distance equal to, $$T \sin\theta \left(1 - \frac{\cos\theta}{\sqrt{n^2 - \sin^2\theta}}\right),$$

where T is the thickness of plate 202, n is its refractive index, and θ is the angle of incidence on plate 202, assuming the surrounding medium has refractive index of 1 (e.g. air or vacuum). The displacement of beam 204 is in the same plane as the angle of incidence. A wedge between the input and output surfaces, if present, only introduces an angular deviation of beam 204 in the plane of the wedge angle, approximately independent of the angle of incidence. FIG. 2a shows an untilted translation plate 202, so output beam 206 is undeviated with respect to input beam 204. FIG. 2b shows translation plate 202 having a clockwise tilt, so output beam 208 is shifted to the right with respect to input beam 204. Similarly, FIG. 2c shows translation plate 202 having a counter-clockwise tilt, so output beam 210 is shifted to the left with respect to input beam 204. Such adjustment of the beam position can be done in both lateral directions (e.g., x and y directions for a z-propagating beam), thereby providing two degrees of freedom.

FIGS. 3a-c show adjustment of beam angle by translating a weak focusing element. In each of these examples, an input beam 304 passes through a positive weak focusing element 302. Translation of weak focusing element 302 changes the angle of beam 304 by an amount equal to, $r \times d_w$, where $d_w = 1/f_w$ is the power and r is the lateral displacement of weak focusing element 302. The change in the angle of beam 304 is in the same plane as the translation of weak focusing element 302. FIG. 3a shows a centered weak focusing element 302, so output beam 306 is undeviated with respect to input beam 304. FIG. 3b shows weak focusing element 302 shifted to the right with respect to beam 304, so output beam 308 is tilted to the right with respect to input beam 304. Similarly, FIG. 3c shows weak focusing element 302 shifted to the left with respect to beam 304, so output beam 310 is tilted to the left with respect to input beam 304. Such adjustment of the beam angle can be done in both lateral directions (e.g., x and y directions for a z-propagating beam), thereby providing two degrees of freedom.

FIGS. 3d-f also show adjustment of beam angle by translating a weak focusing element. In each of these examples, an input beam 304 passes through a negative weak focusing element 312. FIG. 3d shows a centered weak focusing element 312, so output beam 306 is undeviated with respect to input beam 304. FIG. 3e shows weak focusing element 312 shifted to the left with respect to beam 304, so output beam 308 is tilted to the right with respect to input beam 304. Similarly, FIG. 3f shows weak focusing element 312 shifted to the right with respect to beam 304, so output beam 310 is tilted to the left with respect to input beam 304. Thus the weak focusing element (e.g., 110 on FIG. 1) can be either positive or negative in practicing the invention.

FIGS. 4a-c show adjustment of beam size by longitudinally translating a weak positive lens. In each of these examples, an input beam 408 is emitted from a strong focusing element 402 and passes through a weak focusing element 404 to provide an output beam. FIG. 4a shows a weak lens 404 in a nominal position, and output beam 410 incident on cavity input coupler 406 (e.g., a mirror). FIG. 4b shows weak lens 404 shifted toward strong focusing element 402, thereby moving the waist of output beam 412 in the same direction. In this example, the beam size at input coupler 406 decreases. Similarly, FIG. 4c shows weak lens 404 shifted away from strong focusing element 402, thereby moving the waist of beam 414 in the same direction. Here the beam size at input coupler 406 increases.

It is also possible for the relation between the change of longitudinal position of lens 404 and the increase or decrease of beam size at input coupler 406 to be opposite to that shown on FIGS. 4a-c. For example, FIGS. 5a-c also show adjustment of beam size by longitudinally translating a weak positive lens. In each of these examples, an input beam 508 is emitted from a strong focusing element 402 and passes through a weak focusing element 404 to provide an output beam. FIG. 5a shows a weak lens 404 in a nominal position, and output beam 510 incident on cavity input coupler 406 (e.g., a mirror). FIG. 5b shows weak lens 404 shifted toward strong focusing element 402, thereby moving the waist of output beam 512 in the opposite direction. In this example, the beam size at input coupler 406 increases. Similarly, FIG. 5c shows weak lens 404 shifted away from strong focusing element 402, thereby moving the waist of beam 514 in the opposite direction. Here the beam size at input coupler 406 decreases.

The principles of such beam shaping are well known to art workers, as are methods for detailed design for any particular case. In practicing the present invention, it is preferred for the longitudinal adjustment range of the weak focusing element to provide a range of beam waist positions that is sufficiently large to enable a match of beam waist size and location between the lowest order cavity mode and the beam incident on the cavity.

In some cases, the lowest order cavity mode may not have the same beam profile in the two transverse directions, e.g. as a result of fabrication tolerances and/or off-axis incidence on an optical surface inside the cavity. Such a cavity mode is astigmatic, so mode matching to such a cavity can be improved by providing an input beam that at least approximately has the same kind and amount of astigmatism. Astigmatism of second beam 140 can be provided in the embodiment of FIG. 1 by tilting weak focusing element 110 with respect to the beam. The astigmatism introduced by tilting a curved surface with respect to an optical beam is known in the art (e.g., as described in "Lasers" by Siegman on page 586). The need for such an astigmatic adjustment may also arise from an imperfect fiber facet or imperfect alignment of the strong lens 108, causing beam 140 in FIG. 1 to have an elliptical cross-section and/or astigmatic focusing.

Such tilting of the weak focusing element can be regarded as providing a differential adjustment of beam size in the tangential and sagittal planes at the resonator input, as shown in the example of FIGS. 6a-c. FIG. 6a shows an untilted configuration, where beam 608 is emitted from strong focusing element 402 and passes through weak lens 404 to impinge on cavity input coupler 406 as beam 610. FIGS. 6b-c show tangential and sagittal views, respectively, of a configuration in which the weak lens 404 is tilted with respect to the beam. The profiles of the beam in the tangential plane (612) and the sagittal plane (614) differ (e.g., as shown), thereby providing a differential adjustment of beam size at cavity input coupler 406. Alternatively, this can also be regarded as providing a differential adjustment of beam waist position relative to the cavity.

In this example, the tangential and sagittal planes are defined with respect to lens tilt as follows: the sagittal plane includes the axis of lens rotation, while the tangential plane is perpendicular to the axis of lens rotation. Thus for a z-propagating beam and a lens tilt that is a rotation about the y axis, the tangential plane (FIG. 6b) is the x-z plane, and the sagittal plane (FIG. 6c) is the y-z plane.

Methods for adjusting the positions and angles of elements 110 and 114 of FIG. 1 during assembly are well known in the art. Methods of fixing the positions of these elements once a configuration minimizing excitation of higher order cavity modes has been identified are also well known in the art.

The invention claimed is:

1. An optical subsystem for cavity-enhanced spectroscopy, the optical subsystem comprising:
   a source of optical radiation providing a first beam of optical radiation;
   a strong focusing element disposed to receive the first beam of optical radiation and to provide a second beam of optical radiation;
   an optical resonator receiving the second beam, wherein the optical resonator has a lowest order mode and also has one or more higher order modes distinct from the lowest order mode;
   a weak focusing element disposed on a path of the second beam between the strong focusing element and the optical resonator, wherein a magnitude of an optical power of the weak focusing element is substantially smaller than a magnitude of an optical power of the strong focusing element, and wherein the combination of the strong focusing element and the weak focusing element provides an exact or approximate mode match between the second beam and the lowest order mode of the optical resonator;
   a translation plate disposed on the path of the second beam between the strong focusing element and the optical resonator;
   wherein positions and angles of the weak focusing element and translation plate are fixed during assembly of the optical subsystem to minimize or approximately minimize excitation of the higher order modes of the optical resonator by the second beam while coupling the second beam to the lowest order mode.

2. The subsystem of claim 1, wherein a position of said strong focusing element and a position of said optical resonator are fixed prior to fixing positions of said weak focusing element and said translation plate during assembly of said optical subsystem.

3. The subsystem of claim 2 wherein said excitation of the higher order modes of the optical resonator by said second beam is minimized or approximately minimized during assembly by adjusting said positions and angles of said weak focusing element and said translation plate prior to fixing said positions and angles of said weak focusing element and said translation plate.

4. The subsystem of claim 1, wherein angular adjustment of said second beam at said optical resonator is primarily performed by adjusting the lateral position of said weak focusing element with respect to said second beam.

5. The subsystem of claim 1, wherein adjustment of a beam size of said second beam at said optical resonator is primarily performed by adjusting the longitudinal position of said weak focusing element with respect to said second beam.

6. The subsystem of claim 5, wherein differential adjustment of a beam size of said second beam in two transverse planes at said optical resonator is primarily performed by adjusting said angles of said weak focusing element with respect to said second beam.

7. The subsystem of claim 1, wherein adjustment of the position of said second beam at said optical resonator is primarily performed by adjusting said angles of said translation plate with respect to said second beam.

8. The subsystem of claim 1, wherein said translation plate is disposed between said weak focusing element and said optical resonator.

9. The subsystem of claim 8, further comprising an optical isolator disposed on said second beam path between said weak focusing element and said translation plate.

10. The subsystem of claim 1, wherein said optical source comprises a source selected from the group consisting of lasers, diode lasers, standard single mode fiber (SMF) coupled lasers, SMF coupled diode lasers, polarization maintaining (PM) fiber coupled lasers and PM fiber coupled diode lasers.

11. The subsystem of claim 1, wherein said weak focusing element has a positive optical power.

12. The subsystem of claim 1, wherein said weak focusing element has a negative optical power.

13. The subsystem of claim 1, wherein a magnitude of said optical power of said weak focusing element is between about 0.01 and 0.2 times a magnitude of said optical power of said strong focusing element.

14. The subsystem of claim 1, wherein said translation plate comprises a material selected from the group consisting of glass and fused silica.

15. The subsystem of claim 1, further comprising an optical bench, wherein said optical resonator, said strong focusing element, said weak focusing element and said translation plate are all affixed to the optical bench.

16. The subsystem of claim 15, wherein said optical bench and said strong focusing element have substantially the same coefficients of thermal expansion.

17. The subsystem of claim 15, wherein said optical resonator comprises two or more resonator optical elements affixed to a mechanical housing.

18. The subsystem of claim 17, wherein said mechanical housing and said optical bench both comprise FeNi36.

19. The subsystem of claim 1, wherein said strong focusing element comprises a collimator.

20. The subsystem of claim 1, where said weak focusing element comprises a lens.

\* \* \* \* \*